United States Patent
Barone et al.

(10) Patent No.: US 11,793,744 B2
(45) Date of Patent: Oct. 24, 2023

(54) COSMETIC PRODUCTS INCLUDING BIS-CARBOXY SILICONE POLYMER COMPONENT

(71) Applicant: Coty Inc., New York, NY (US)

(72) Inventors: Salvatore J. Barone, Vero Beach, FL (US); Lethu Nguyen, Colonia, NJ (US); Tina Schaefer, Franklin, NJ (US)

(73) Assignee: COTY, INC., New York, NY (US)

(*) Notice: Subject to any disclaimer, the term of this patent is extended or adjusted under 35 U.S.C. 154(b) by 29 days.

(21) Appl. No.: 16/641,767

(22) PCT Filed: Aug. 23, 2018

(86) PCT No.: PCT/US2018/047779
§ 371 (c)(1),
(2) Date: Feb. 25, 2020

(87) PCT Pub. No.: WO2019/040767
PCT Pub. Date: Feb. 28, 2019

(65) Prior Publication Data
US 2020/0390682 A1    Dec. 17, 2020

Related U.S. Application Data

(60) Provisional application No. 62/550,187, filed on Aug. 25, 2017.

(51) Int. Cl.
*A61K 8/891* (2006.01)
*A61K 8/02* (2006.01)
*A61Q 1/06* (2006.01)

(52) U.S. Cl.
CPC ............ *A61K 8/891* (2013.01); *A61K 8/0229* (2013.01); *A61Q 1/06* (2013.01); *A61K 2800/42* (2013.01)

(58) Field of Classification Search
None
See application file for complete search history.

(56) References Cited

U.S. PATENT DOCUMENTS

| | | |
|---|---|---|
| 6,451,295 B1 | 9/2002 | Cai et al. |
| 8,513,174 B2 | 8/2013 | Araki et al. |
| 9,181,401 B2 | 11/2015 | Parakka et al. |
| 2013/0164235 A1* | 6/2013 | Lebre-Lemonnier ........................ A61K 8/895 424/70.7 |
| 2015/0157996 A1 | 6/2015 | Dussaud et al. |

FOREIGN PATENT DOCUMENTS

WO    WO-2019040767 A1    2/2019

OTHER PUBLICATIONS

Silform INX fluid (see IDS filed Feb. 25, 2015).*
Silform INX Fluid Feb. 25, 2015.*
"Silform INX fluid", Momentive Marketing Bulletin 2015.*
Jeen International Corporation.*
Cream Dictionary definition from Oxford Languages.*
"Big Volume Mascara", GNPD Mintel Database; Database accession No. 5040111, (Aug. 1, 2017), 3 pgs.
"International Application Serial No. PCT/US2018/047779, International Search Report dated Oct. 24, 2018", 3 pgs.
"International Application Serial No. PCT/US2018/047779, Written Opinion dated Oct. 24, 2018", 5 pgs.
"Silform INX fluid", Momentive Marketing Bulletin, [Online] Retrieved from the Internet : <http://www.essentialingredients.com/pdf/SilFormINXmarketi ngbrochure.pdf>, (Feb. 2, 2015), 12 pgs.
"International Application Serial No. PCT/US2018/047779, International Preliminary Report on Patentability dated Mar. 5, 2020", 7 pgs.

* cited by examiner

*Primary Examiner* — Danah Al-Awadi
(74) *Attorney, Agent, or Firm* — SCHWEGMAN LUNDBERG & WOESSNER, P.A.

(57) ABSTRACT

The present disclosure provides a free-standing cosmetic stick or a liquid cosmetic. The free-standing cosmetic stick or liquid cosmetic includes a bis-carboxy silicone polymer component, one or more coloring agents, and one or more constituents for rendering the formulation into a solid stick or liquid cosmetic.

2 Claims, No Drawings

COSMETIC PRODUCTS INCLUDING BIS-CARBOXY SILICONE POLYMER COMPONENT

CROSS-REFERENCE TO RELATED APPLICATION

This application is a U.S. National Stage Filing under 35 U.S.C. 371 from International Application No. PCT/US2018/047779, filed on Aug. 23, 2018, and published as WO 2019/040767 on Feb. 28, 2019, which application claims the benefit of priority to U.S. Provisional Patent Application Ser. No. 62/550,187 entitled "FREE-STANDING COSMETIC STICKS INCLUDING BIS-CARBOXY SILICONE POLYMER COMPONENT," filed Aug. 25, 2017, the disclosures of which are incorporated herein in their entirety by reference.

FIELD

Inventive subject matter disclosed herein relates to lipstick and other anhydrous cosmetic embodiments and method embodiments for making lipstick and other anhydrous cosmetics having shiny, transfer resistant properties.

BACKGROUND

Materials of lipstick or gloss applied to a person's lips are designed to last for a suitable amount of time. While applied, the material should be comfortable to the user. Some materials can be uncomfortable in that they can cause the user's lips to feel dry. It is desirable therefore to produce materials that are comfortable to the user.

SUMMARY OF THE DISCLOSURE

The present disclosure provides a free-standing cosmetic stick or liquid cosmetic. The free-standing cosmetic stick or liquid cosmetic includes a bis-carboxy silicone polymer component, one or more coloring agents, and one or more constituents for rendering the formulation into a solid stick.

The present disclosure further provides a method of making a free-standing cosmetic stick or liquid cosmetic including a bis-carboxy silicone polymer component, one or more coloring agents, and one or more constituents for rendering the formulation into a solid stick or liquid cosmetic. The method includes preparing a formulation comprising the bis-carboxy silicone polymer component and one or more coloring agents. The method further includes heating the formulation and forming the formulation into a stick shape or liquid cosmetic to make a formed stick shape. The method further includes cooling the formed stick. or liquid cosmetic The present disclosure further provides a cosmetic formulation comprising:

| Raw Material Name | wt % |
| --- | --- |
| BIS-CARBOXYDECYL DIMETHICONE | 7-13 |
| C9-12 ALKANE | 7-13 |
| CAPRYLYL GLYCOL | 0.05-0.70 |
| COCO-CAPRYLATE/CAPRATE | 0.5-2.0 |
| D&C RED NO. 7 CALCIUM LAKE | 2-6 |
| FD&C YELLOW NO. 5 ALUMINUM LAKE | 0.5-1.5 |
| FRAGRANCE | 0.05-0.70 |
| HDI/TRIMETHYLOL HEXYLLACTONE CROSSPOLYMER | 0.50-2.00 |
| IRON OXIDES | 0.5-1.5 |
| ISODODECANE | 30-45 |
| MICA | 0.50-1.50 |
| PHENOXYETHANOL | 0.10-0.70 |
| PHENYL TRIMETHICONE | 2.00-6.00 |
| POLYETHYLENE | 5.00-15.00 |
| POLYPROPYLENE | 1.00-7.00 |
| QUATERNIUM-90 MONTMORILLONITE | 1.00-2.00 |
| QUATERNIUM-90 SEPIOLITE | 2.00-7.00 |
| SILICA | 0.01-0.070 |
| SILICA DIMETHYL SILYLATE | 0.20-0.70 |
| TITANIUM DIOXIDE | 0.50-1.50 |
| TRIETHOXYCAPRYLYLSILANE | 0.02-0.07 |
| TRIMETHYLSILOXYSILICATE | 1.5-4.5 |
| UNDECYLENIC ACID | 0.04-1.00 |

The present disclosure further provides a cosmetic formulation comprising:

| Raw Material Name | wt % |
| --- | --- |
| BHT | 0.000001-0.000006 |
| BIS-CARBOXYDECYL DIMETHICONE | 10.00-20.00 |
| C9-12 ALKANE | 14.00-20.00 |
| CAPRYLYL GLYCOL | 0.05-3.50 |
| COCO-CAPRYLATE/CAPRATE | 1.00-2.50 |
| D&C RED NO. 7 CALCIUM LAKE | 1.00-3.00 |
| FD&C YELLOW NO. 5 ALUMINUM LAKE | 1.50-3.50 |
| FRAGRANCE | 0.02-0.60 |
| HDI/TRIMETHYLOL HEXYLLACTONE CROSSPOLYMER | 1.00-2.00 |
| IRON OXIDES | 1.00-3.00 |
| ISODODECANE | 20.00-25.00 |
| MICA | 0.10-0.70 |
| OZOKERITE | 1.00-3.00 |
| PHENOXYETHANOL | 0.10-0.40 |
| PHENYL TRIMETHICONE | 2.00-7.00 |
| POLYETHYLENE | 10.00-19.00 |
| QUATERNIUM-90 MONTMORILLONITE | 0.50-1.00 |
| QUATERNIUM-90 SEPIOLITE | 0.15-0.40 |
| SILICA | 0.01-0.07 |
| TITANIUM DIOXIDE | 3.00-9.00 |
| TRIETHOXYCAPRYLYLSILANE | 0.10-0.50 |
| TRIMETHYLSILOXYSILICATE | 0.10-0.90 |
| UNDECYLENIC ACID | 0.05-0.20 |

There are various reasons to use the free-standing cosmetic sticks or cosmetic formulations of the present disclosure including the following non-limiting reasons. One reason is that the presence of anon-neutralized bis-carboxy silicone polymer component (e.g., bis-carboxydecyl dimethicone) makes the cosmetic application feel more comfortable and less dry on a user's lips than a corresponding formulation including a neutralized bis-carboxy silicone polymer.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O) CH$_2$C(O)R, C(S)R, C(O)OR, OC(O)R, C(O)N(R)$_2$, OC(O) N(R)$_2$, C(S)N(R)$_2$, (CH$_2$)$_{0-2}$N(R)C(O)R, (CH$_2$)$_{0-2}$N(R)N (R)$_2$, N(R)N(R)C(O)R, N(R)N(R)C(O)OR, N(R)N(R)CON (R)$_2$, N(R)SO$_2$R, N(R)SO$_2$N(R)$_2$, N(R)C(O)OR, N(R)C(O) R, N(R)C(S)R, N(R)C(O)N(R)$_2$, N(R)C(S)N(R)$_2$, N(COR) COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term, "free of neutralization" as used herein refers to a bis-carboxy polymer component that is disposed in a non-aqueous carrier or emulsifier substantially free of a base, such as sodium hydroxide or potassium hydroxide.

The polymers described herein can terminate in any suitable way. In some embodiments, the polymers can terminate with an end group that is independently chosen from a suitable polymerization initiator, —H, —OH, a substituted or unsubstituted ($C_1$-$C_{20}$)hydrocarbyl (e.g., ($C_1$-$C_{10}$)alkyl or ($C_6$-$C_{20}$)aryl) interrupted with 0, 1, 2, or 3 groups independently selected from —O—, substituted or unsubstituted —NH—, and —S—, a poly(substituted or unsubstituted ($C_1$-$C_{20}$)hydrocarbyloxy), and a poly(substituted or unsubstituted ($C_1$-$C_{20}$)hydrocarbylamino).

The term "stick" as used herein, refers to cosmetic compositions molded into the form of a stick. For some embodiments, the compositions are heated until molten and then poured into a mold and cooled. Stick embodiments also include anhydrous compositions capable of being formed into sticks.

The term "COCO-CAPRYLATE/CAPRATE" is understood to refer to a mixture of esters of coconut alcohol with caprylic acid and capric acid.

The term "D&C RED NO. 7 CALCIUM LAKE" is understood to refer to a calcium salt of 4-(o-sulfo-p-tolylazo)-3-hydroxy-2-naphthoic acid.

The term "FD&C YELLOW NO. 5 ALUMINUM LAKE" is understood to refer to a yellow colorant The term "QUATERNIUM-90 MONTMORILLONITE" is understood to refer to a reaction product of bentonite and quaternium-90.

The term "BHT" is understood to refer to butylated hydroxytoluene

The term "OZOKERITE" is understood to refer a naturally occurring mineral wax or paraffin.

Embodiments of the invention are described in sufficient detail to enable those skilled in the art to practice the invention. Other embodiments may be utilized and structural, logical, chemical, and other changes may be made without departing from the spirit or scope of the invention discussed herein. The following detailed description is, therefore, not to be taken in a limiting sense, and the scope of the invention discussed herein is defined only by the appended claims.

According to various embodiments, a free-standing cosmetic stick or liquid cosmetic (e.g., lip stick or lip gloss) can include many different components. For example, the free-standing cosmetic stick or liquid cosmetic can include a bis-carboxy silicone polymer component. The bis-carboxy polymer component can include one or more polymers. The one or more polymers can be in a range of from about 5 wt % to about 30 wt % of the bis-carboxy silicone polymer component, about 10 wt % to about 20 wt %, or less than, equal to, or greater than about 5 w %, 6, 7, 8, 9, 10, 11, 12, 13, 14, 15, 16, 17, 18, 19, or about 20 wt %. The bis-carboxy polymer component is disposed in a non-aqueous carrier or emulsifier and is substantially free of a base (e.g., sodium hydroxide or potassium hydroxide). The bis-carboxy polymer component is accordingly free of neutralization. As understood, neutralization is a chemical reaction in which an acid and a base react quantitatively with each other. As an example, in a reaction in water, neutralization results in there being no excess of hydrogen or hydroxide ions present in the solution.

It has been surprisingly found that including the bis-carboxy silicone polymer in the free-standing cosmetic stick or cosmetic liquid results in a product that users find more comfortable than a corresponding free-standing cosmetic stick or cosmetic liquid that includes a neutralized bis-carboxy silicone polymer. For example, users have found that the instant free-standing cosmetic sticks or cosmetic liquids can provide increased comfort and feel less drying. This result is surprising in part because bis-carboxy silicone polymers are typically included in formulations in a neutralized or aqueous state.

According to various embodiments, the bis-carboxy silicone polymer can include one or more polymers. The one or more polymers can be in a range of from about 8 wt % to about 20 wt % of the free-standing cosmetic stick, or about 9 wt % to about 15 wt %, or less than, equal to, or greater than about 8 wt %, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 wt %.

According to various embodiments, the one or more polymers can include a compound having a structure according to Formula I:

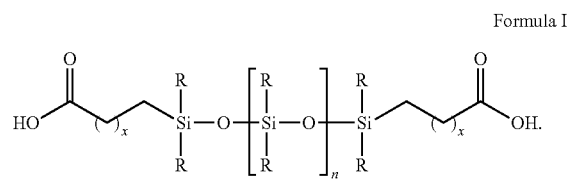

Formula I

In Formula I, at each occurrence R is independently chosen from substituted or unsubstituted —OH, ($C_1$-$C_{40}$)alkyl, ($C_1$-$C_{40}$)alkenyl, ($C_1$-$C_{40}$)alkoxy, ($C_1$-$C_{40}$)haloalkyl, and ($C_4$-$C_{12}$)aryl. At each occurrence, the value x is any positive integer equal to or greater than 1 and n is any positive integer equal to or greater than 1. As an example, the value x can be in range of from about 1 to about 20, about 8 to about 10, or less than, equal to, or greater than about 1, 2, 3, 4, 5, 6, 7, 8, 9, 10. As an example, the value n can be in a range of from about 1 to about 100, about 20 to about 50, or less than, equal to, or greater than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100.

In some embodiments the free-standing color cosmetic stick or cosmetic liquids includes a compound having the structure according to Formula II:

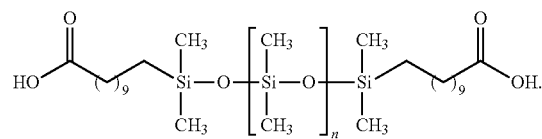

The structure according to Formula II, can be referred to as bis-carboxydecyl dimethicone.

In addition to the bis-carboxy silicone polymer component the free-standing color cosmetic stick or cosmetic liquids can include components to impart color in the formulation. Suitable examples of color forming components include silica, kaolin, talc, mica, titanium dioxide, iron oxide, black oxide, and polymethylsisesquioxane.

The free-standing cosmetic stick or cosmetic liquids can further include components such as, isoamyl (isopentyl) laurate. Isoamyl laurate is a multifunctional emollient, which provides an excellent silicone feeling and a good skin compatibility. The free-standing cosmetic stick can further include ingredients such as petrolatum is also known as perfecta; saxoline; VASELINE; PARAFFIN; PARAFIN; cosmoline; FEMA 3216; WAX WHITE; PARAFFINE. Petrolatum has a CAS No. of 8009-03-8. Petrolatum is a purified mixture of semisolid saturated hydrocarbons having the general formula $C(n)H(2n+2)$.

The free-standing cosmetic stick can also include microcrystalline wax. If present, the microcrystalline wax is a hardening wax and has a melting point ranging from 85° C. to 95° C. A hardness of the microcrystalline wax ranges from 6 to 14 decimillimeters (dmm). The microcrystalline wax is added to the free-standing cosmetic stick formulation as a granule, pellet, slab or liquid bulk.

Another ingredient that can be added is ozokerite wax, which is a naturally occurring, light yellow to dark brown mineral wax composed of solid paraffinic hydrocarbons.

In some examples, it may be desirable for free-standing cosmetic stick or cosmetic liquids to be color free. This can be the case, for example, when the free-standing cosmetic stick or cosmetic liquids is used as a foundation. In these examples petrolatum can be in a range of from 5 wt % to about 6 wt %.

In additional examples, the free-standing cosmetic stick or cosmetic liquids can also include Carnauba wax and Candelilla wax in concentrations that total about 4 wt % to about 6 wt % of the free-standing stick formulation. A formulation that includes dimethicone/divinyl dimethicone/Silsesquioxane crosspolymer; Copernecia and Cerafera wax is added to the foundation and blush formulation embodiments in a concentration of 3 to 4 percent by weight to impart an effective degree of transfer to a user's skin.

In additional examples, the free-standing cosmetic stick or cosmetic liquid formulation can include polyglycerol-3 diisostearate. The polyglycerol-3 diisostearate acts as a thickener and an emulsifier. In additional examples, the free-standing cosmetic stick or cosmetic liquid formulation is free of volatile components.

Specific formulations of the free-standing cosmetic stick or cosmetic liquid formulation embodiments are as follows and are presented to exemplify embodiments but not limit them. According to various embodiments a formulation of the free-standing cosmetic stick or cosmetic liquid formulation can include:

| Raw Material Name | wt % |
| --- | --- |
| BIS-CARBOXYDECYL DIMETHICONE | 7-13 |
| C9-12 ALKANE | 7-13 |
| CAPRYLYL GLYCOL | 0.05-0.70 |
| COCO-CAPRYLATE/CAPRATE | 0.5-2.0 |
| D&C RED NO. 7 CALCIUM LAKE | 2-6 |
| FD&C YELLOW NO. 5 ALUMINUM LAKE | 0.5-1.5 |
| FRAGRANCE | 0.05-0.70 |
| HDI/TRIMETHYLOL HEXYLLACTONE CROSSPOLYMER | 0.50-2.00 |
| IRON OXIDES | 0.5-1.5 |
| ISODODECANE | 30-45 |
| MICA | 0.50-1.50 |
| PHENOXYETHANOL | 0.10-0.70 |
| PHENYL TRIMETHICONE | 2.00-6.00 |
| POLYETHYLENE | 5.00-15.00 |
| POLYPROPYLENE | 1.00-7.00 |
| QUATERNIUM-90 MONTMORILLONITE | 1.00-2.00 |
| QUATERNIUM-90 SEPIOLITE | 2.00-7.00 |
| SILICA | 0.01-0.070 |
| SILICA DIMETHYL SILYLATE | 0.20-0.70 |
| TITANIUM DIOXIDE | 0.50-1.50 |
| TRIETHOXYCAPRYLYLSILANE | 0.02-0.07 |
| TRIMETHYLSILOXYSILICATE | 1.5-4.5 |
| UNDECYLENIC ACID | 0.04-1.00 |

According to various embodiments, another formulation of the free-standing cosmetic stick or cosmetic liquid formulation can include:

| Raw Material Name | wt % |
| --- | --- |
| BHT | 0.000001-0.000006 |
| BIS-CARBOXYDECYL DIMETHICONE | 10.00-20.00 |
| C9-12 ALKANE | 14.00-20.00 |
| CAPRYLYL GLYCOL | 0.05-3.50 |
| COCO-CAPRYLATE/CAPRATE | 1.00-2.50 |
| D&C RED NO. 7 CALCIUM LAKE | 1.00-3.00 |
| FD&C YELLOW NO. 5 ALUMINUM LAKE | 1.50-3.50 |
| FRAGRANCE | 0.02-0.60 |
| HDI/TRIMETHYLOL HEXYLLACTONE CROSSPOLYMER | 1.00-2.00 |
| IRON OXIDES | 1.00-3.00 |
| ISODODECANE | 20.00-25.00 |
| MICA | 0.10-0.70 |
| OZOKERITE | 1.00-3.00 |
| PHENOXYETHANOL | 0.10-0.40 |
| PHENYL TRIMETHICONE | 2.00-7.00 |
| POLYETHYLENE | 10.00-19.00 |
| QUATERNIUM-90 MONTMORILLONITE | 0.50-1.00 |
| QUATERNIUM-90 SEPIOLITE | 0.15-0.40 |
| SILICA | 0.01-0.07 |
| TITANIUM DIOXIDE | 3.00-9.00 |
| TRIETHOXYCAPRYLYLSILANE | 0.10-0.50 |
| TRIMETHYLSILOXYSILICATE | 0.10-0.90 |
| UNDECYLENIC ACID | 0.05-0.20 |

According to various embodiments, another formulation of the free-standing cosmetic stick or cosmetic liquid formulation can include bis-carboxydecyl dimethicone; a colorant or collection of colorants; a structuring agent or collection of structuring agents; a preservative or collection of preservatives; a solvent or collection of solvents; a gelling agent or collection of gelling agents.

According to various embodiments, another formulation of the free-standing cosmetic stick or cosmetic liquid formulation can include:

| Raw Material Name | wt % |
| --- | --- |
| BIS-CARBOXYDECYL DIMETHICONE | 16.00% |
| Colorant | 11.4%-17.00% |
| Structuring Agent | 14.80%-22.70% |
| preservative | 0.20%-0.50% |
| solvent | 34.40%-51.6% |

According to various embodiments, another formulation of the free-standing cosmetic stick or cosmetic liquid formulation can include:

| Raw Material Name | wt % |
|---|---|
| BIS-CARBOXYDECYL DIMETHICONE | 13.00% |
| Colorant | 6.40%-9.60% |
| Gelling Agent | 13.60%-20.50% |
| preservative | 0.20%-0.50% |
| solvent | 39.70%-59.6% |

According to various embodiments, another formulation of the free-standing cosmetic stick or cosmetic liquid formulation can include:

| Raw Material Name | wt % |
|---|---|
| BIS-CARBOXYDECYL DIMETHICONE | 14.00% |
| Colorant | 7.20%-10.80% |
| Gelling Agent | 4.8%-7.20% |
| Structuring Agent | 8.00%-12.00% |
| preservative | 0.20%-0.50% |
| solvent | 31.00%-49.00% |

Examples of solvents that may be included in the solvent component include a C9-C12 Alkane and isododecane. Examples of structuring agents include hdi/trimethylol hexyllactone crosspolymer, polyethylene, silica, triethoxycaprylylsilane, and trimethylsiloxysilicate. Examples of gelling agents include polypropylene, quaternium-90 montmorillonite, and quaternium-90 sepiolite. Examples of preservatives include phenoxyethanol. Examples of colorants include D&C red no. 7 calcium lake, Fd&C yellow no. 5 aluminum lake, and titanium dioxide.

The free-standing cosmetic stick or cosmetic liquid formulation can be made according to any suitable method. An example of a suitable method includes making the free-standing cosmetic stick or cosmetic liquid formulation with a hot pour technique. The hot pour technique can be especially useful to formulate free-standing cosmetic sticks without any volatile ingredients. The method can include preparing a formulation including any combination of the ingredients described herein. The ingredients, including the non-neutralized bis-carboxy silicone polymer component, can be mixed together and heated to form a molten mixture. The mixture can be heated in a mold, that generally conforms to a desired shape of the stick (e.g., a generally bullet shaped stick), or the mixture can be heated and subsequently deposited in the mold. After a suitable amount of time, the mold is cooled to harden the mixture. The hardened mixture can, optimally, be heat treated with a flame. Heat treating can help to remove imperfections in the stick or give a shiny finish.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

ADDITIONAL EMBODIMENTS

The following exemplary embodiments are provided, the numbering of which is not to be construed as designating levels of importance:

Embodiment 1 provides a free-standing cosmetic stick or liquid comprising:
a bis-carboxy silicone polymer component;
one or more coloring agents; and
one or more constituents for rendering the formulation into a solid stick.

Embodiment 2 provides the free-standing cosmetic stick or liquid of Embodiment 1, wherein the bis-carboxy silicone polymer component comprises one or more polymers.

Embodiment 3 provides the free-standing cosmetic stick or liquid of Embodiment 2, wherein the one or more polymers are in a range of from about 50 wt % to about 100 wt % of the bis-carboxy silicone polymer component.

Embodiment 4 provides the free-standing cosmetic stick or liquid of any one of Embodiments 2 or 3, wherein the one or more polymers are substantially free of neutralization.

Embodiment 5 provides the free-standing cosmetic stick or liquid of any one of Embodiments 1-4, wherein the bis-carboxy silicone polymer component is disposed in a non-aqueous solution.

Embodiment 6 provides the free-standing cosmetic stick or liquid of any one of Embodiments 1-6, wherein the bis-carboxy silicone polymer is free of a base.

Embodiment 7 provides the free-standing cosmetic stick or liquid of Embodiment 6, wherein the base is chosen from sodium hydroxide, potassium hydroxide, or a mixture thereof.

Embodiment 8 provides the free-standing cosmetic stick or liquid of any one of Embodiments 1-7, wherein the bis-carboxy silicone polymer component comprises one or more polymers having a structure according to Formula I:

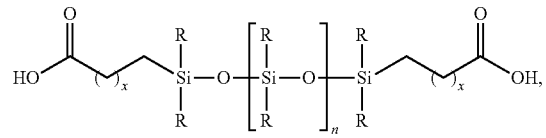

wherein at each occurrence R is independently chosen from substituted or unsubstituted —OH, $(C_1$-$C_{40})$alkyl, $(C_1$-$C_{40})$alkenyl, $(C_1$-$C_{40})$alkoxy, $(C_1$-$C_{40})$haloalkyl, and $(C_4$-$C_{12})$aryl the value x is any positive integer equal to or greater than 1 and n is any positive integer equal to or greater than 1.

Embodiment 9 provides the free-standing cosmetic stick or liquid of any one of Embodiments 1-8, wherein the bis-carboxy silicone polymer comprises one or more polymers having a structure according to Formula II:

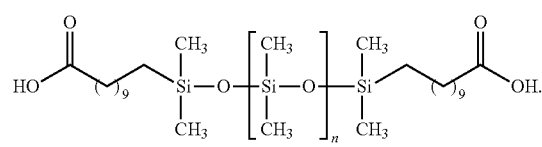

Embodiment 10 provides the free-standing cosmetic stick or liquid of any one of Embodiments 1-9, wherein a concentration the bis-carboxy silicone polymer is in a range of from about 5 wt % to about 40 wt %.

Embodiment 11 provides the free-standing cosmetic stick or liquid of any one of Embodiments 1-9, wherein a concentration the bis-carboxy silicone polymer is in a range of from about 8 wt % to about 20 wt %.

Embodiment 12 provides the free-standing cosmetic stick or liquid of any one of Embodiments 1-11, wherein the bis-carboxy silicone polymer is bis-carboxydecyl dimethicone.

Embodiment 13 provides the free-standing cosmetic stick of Embodiment 12, wherein the free-standing cosmetic stick comprises:

| Raw Material Name | wt % |
| --- | --- |
| BIS-CARBOXYDECYL DIMETHICONE | 7-13 |
| C9-12 ALKANE | 7-13 |
| CAPRYLYL GLYCOL | 0.05-0.70 |
| COCO-CAPRYLATE/CAPRATE | 0.5-2.0 |
| D&C RED NO. 7 CALCIUM LAKE | 2-6 |
| FD&C YELLOW NO. 5 ALUMINUM LAKE | 0.5-1.5 |
| FRAGRANCE | 0.05-0.70 |
| HDI/TRIMETHYLOL HEXYLLACTONE CROSSPOLYMER | 0.50-2.00 |
| IRON OXIDES | 0.5-1.5 |
| ISODODECANE | 30-45 |
| MICA | 0.50-1.50 |
| PHENOXYETHANOL | 0.10-0.70 |
| PHENYL TRIMETHICONE | 2.00-6.00 |
| POLYETHYLENE | 5.00-15.00 |
| POLYPROPYLENE | 1.00-7.00 |
| QUATERNIUM-90 MONTMORILLONITE | 1.00-2.00 |
| QUATERNIUM-90 SEPIOLITE | 2.00-7.00 |
| SILICA | 0.01-0.070 |
| SILICA DINIETHYL SILYLATE | 0.20-0.70 |
| TITANIUM DIOXIDE | 0.50-1.50 |
| TRIETHOXYCAPRYLYLSILANE | 0.02-0.07 |
| TRIMETHYLSILOXYSILICATE | 1.5-4.5 |
| UNDECYLENIC ACID | 0.04-1.00 |

Embodiment 14 provides the free-standing cosmetic stick or liquid of Embodiment 12, wherein the free-standing cosmetic stick comprises:

| Raw Material Name | wt % |
| --- | --- |
| BHT | 0.000001-0.000006 |
| BIS-CARBOXYDECYL DIMETHICONE | 10.00-20.00 |
| C9-12 ALKANE | 14.00-20.00 |
| CAPRYLYL GLYCOL | 0.05-3.50 |
| COCO-CAPRYLATE/CAPRATE | 1.00-2.50 |
| D&C RED NO. 7 CALCIUM LAKE | 1.00-3.00 |
| FD&C YELLOW NO. 5 ALUMINUM LAKE | 1.50-3.50 |
| FRAGRANCE | 0.02-0.60 |
| HDI/TRIMETHYLOL HEXYLLACTONE CROSSPOLYMER | 1.00-2.00 |
| IRON OXIDES | 1.00-3.00 |
| ISODODECANE | 20.00-25.00 |
| MICA | 0.10-0.70 |
| OZOKERITE | 1.00-3.00 |
| PHENOXYETHANOL | 0.10-0.40 |
| PHENYL TRIMETHICONE | 2.00-7.00 |
| POLYETHYLENE | 10.00-19.00 |
| QUATERNIUM-90 MONTMORILLONITE | 0.50-1.00 |
| QUATERNIUM-90 SEPIOLITE | 0.15-0.40 |
| SILICA | 0.01-0.07 |
| TITANIUM DIOXIDE | 3.00-9.00 |
| TRIETHOXYCAPRYLYLSILANE | 0.10-0.50 |
| TRIMETHYLSILOXYSILICATE | 0.10-0.90 |
| UNDECYLENIC ACID | 0.05-0.20 |

Embodiment 15 provides the free-standing cosmetic stick or liquid of any one of Embodiments 1-14, wherein the free-standing cosmetic stick or cosmetic liquid formulation is chosen from lip stick or lip gloss.

Embodiment 16 provides the free-standing cosmetic stick or liquid of any one of Embodiments 4-15, wherein as applied to a user, the free-standing cosmetic stick or liquid is perceived as less drying and more comfortable than a corresponding free-standing cosmetic stick that includes neutralized bis-carboxy silicone polymers.

Embodiment 17 provides a method of making the free-standing cosmetic stick or liquid of any one Embodiments 1-15, the method comprising:
  preparing a formulation comprising:
    the bis-carboxy silicone polymer component; and
    one or more coloring agents; and
  heating the formulation and forming the formulation into a stick shape to make a formed stick shape; and
  cooling the formed stick.

Embodiment 18 provides the method of Embodiment 17, wherein the bis-carboxy silicone component is added to the formulation as a non-aqueous phase.

Embodiment 19 provides a cosmetic formulation comprising:

| Raw Material Name | wt % |
| --- | --- |
| BIS-CARBOXYDECYL DIMETHICONE | 7-13 |
| C9-12 ALKANE | 7-13 |
| CAPRYLYL GLYCOL | 0.05-0.70 |
| COCO-CAPRYLATE/CAPRATE | 0.5-2.0 |
| D&C RED NO. 7 CALCIUM LAKE | 2-6 |
| FD&C YELLOW NO. 5 ALUMINUM LAKE | 0.5-1.5 |
| FRAGRANCE | 0.05-0.70 |
| HDI/TRIMETHYLOL HEXYLLACTONE CROSSPOLYMER | 0.50-2.00 |
| IRON OXIDES | 0.5-1.5 |
| ISODODECANE | 30-45 |
| MICA | 0.50-1.50 |
| PHENOXYETHANOL | 0.10-0.70 |
| PHENYL TRIMETHICONE | 2.00-6.00 |
| POLYETHYLENE | 5.00-15.00 |
| POLYPROPYLENE | 1.00-7.00 |
| QUATERNIUM-90 MONTMORILLONITE | 1.00-2.00 |
| QUATERNIUM-90 SEPIOLITE | 2.00-7.00 |
| SILICA | 0.01-0.070 |
| SILICA DIMETHYL SILYLATE | 0.20-0.70 |
| TITANIUM DIOXIDE | 0.50-1.50 |
| TRIETHOXYCAPRYLYLSILANE | 0.02-0.07 |
| TRIMETHYLSILOXYSILICATE | 1.5-4.5 |
| UNDECYLENIC ACID | 0.04-1.00 |

Embodiment 20 provides a cosmetic formulation comprising:

| Raw Material Name | wt % |
| --- | --- |
| BHT | 0.000001-0.000006 |
| BIS-CARBOXYDECYL DIMETHICONE | 10.00-20.00 |
| C9-12 ALKANE | 14.00-20.00 |
| CAPRYLYL GLYCOL | 0.05-3.50 |
| COCO-CAPRYLATE/CAPRATE | 1.00-2.50 |
| D&C RED NO. 7 CALCIUM LAKE | 1.00-3.00 |
| FD&C YELLOW NO. 5 ALUMINUM LAKE | 1.50-3.50 |
| FRAGRANCE | 0.02-0.60 |
| HDI/TRIMETHYLOL HEXYLLACTONE CROSSPOLYMER | 1.00-2.00 |
| IRON OXIDES | 1.00-3.00 |
| ISODODECANE | 20.00-25.00 |
| MICA | 0.10-0.70 |
| OZOKERITE | 1.00-3.00 |
| PHENOXYETHANOL | 0.10-0.40 |

-continued

| Raw Material Name | wt % |
| --- | --- |
| PHENYL TRIMETHICONE | 2.00-7.00 |
| POLYETHYLENE | 10.00-19.00 |
| QUATERNIUM-90 MONTMORILLONITE | 0.50-1.00 |
| QUATERNIUM-90 SEPIOLITE | 0.15-0.40 |
| SILICA | 0.01-0.07 |
| TITANIUM DIOXIDE | 3.00-9.00 |
| TRIETHOXYCAPRYLYLSILANE | 0.10-0.50 |
| TRIMETHYLSILOXYSILICATE | 0.10-0.90 |
| UNDECYLENIC ACID | 0.05-0.20 |

Embodiment 21 provides a cosmetic formulation comprising:

| Raw Material Name | wt % |
| --- | --- |
| BIS-CARBOXYDECYL DIMETHICONE | 16.00% |
| Colorant | 11.4%-17.00% |
| Structuring Agent | 14.80%-22.70% |
| preservative | 0.20%-0.50% |
| solvent | 34.40%-51.6% |

Embodiment 22 provides a cosmetic formulation comprising:

| Raw Material Name | wt % |
| --- | --- |
| BIS-CARBOXYDECYL DIMETHICONE | 13.00% |
| Colorant | 6.40%-9.60% |
| Gelling Agent | 13.60%-20.50% |
| preservative | 0.20%-0.50% |
| solvent | 39.70%-59.6% |

Embodiment 23 provides a cosmetic formulation comprising:

| Raw Material Name | wt % |
| --- | --- |
| BIS-CARBOXYDECYL DIMETHICONE | 14.00% |
| Colorant | 7.20%-10.80% |
| Gelling Agent | 4.8%-7.20% |
| Structuring Agent | 8.00%-12.00% |
| preservative | 0.20%-0.50% |
| solvent | 31.00%-49.00% |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A cosmetic formulation comprising:
bis-carboxydecyl dimethicone in a range of from 7-13 wt %;
c9-12 alkane in a range of from 7-13 wt %;
caprylyl glycol in a range of from 0.05-0.70 wt %;
coco-caprylate/caprate in a range of from 0.5-2.0 wt %;
d&c red no. 7 calcium lake in a range of from 2-6 wt %;
fd&c yellow no. 5 aluminum lake in a range of from 0.5-1.5 wt %;
fragrance in a range of from 0.05-0.70 wt %;
hdi/trimethylol hexyllactone crosspolymer in a range of from 0.50-2.00 wt %;
iron oxides in a range of from 0.5-1.5 wt %;
isododecane in a range of from 30-45 wt %;
mica in a range of from 0.50-1.50 wt %;
phenoxyethanol in a range of from 0.10-0.70 wt %;
phenyl trimethicone in a range of from 2.00-6.00 wt %;
polyethylene in a range of from 5.00-15.00 wt %;
polypropylene in a range of from 1.00-7.00 wt %;
quaternium-90 montmorillonite in a range of from 1.00-2.00 wt %;
quaternium-90 sepiolite in a range of from 2.00-7.00 wt %;
silica in a range of from 0.01-0.070 wt %;
silica dimethyl silylate in a range of from 0.20-0.70 wt %;
titanium dioxide in a range of from 0.50-1.50 wt %;
triethoxycaprylylsilane in a range of from 0.02-0.07 wt %;
trimethylsiloxysilicate in a range of from 1.5-4.5 wt %; and
undecylenic acid in a range of from 0.04-1.00 wt %.

2. A cosmetic formulation comprising:
bht in a range of from 0.000001-0.000006 wt %;
bis-carboxydecyl dimethicone in a range of from 10.00-20.00 wt %;
c9-12 alkane in a range of from 14.00-20.00 wt %;
caprylyl glycol in a range of from 0.05-3.50 wt %;
coco-caprylate/caprate in a range of from 1.00-2.50 wt %;
d&c red no. 7 calcium lake in a range of from 1.00-3.00 wt %;
fd&c yellow no. 5 aluminum lake in a range of from 1.50-3.50 wt %;
fragrance in a range of from 0.02-0.60 wt %;
hdi/trimethylol hexyllactone crosspolymer in a range of from 1.00-2.00 wt %;
iron oxides in a range of from 1.00-3.00 wt %;
isododecane in a range of from 20.00-25.00 wt %;
mica in a range of from 0.10-0.70 wt %;
ozokerite in a range of from 1.00-3.00 wt %;
phenoxyethanol in a range of from 0.10-0.40 wt %;
phenyl trimethicone in a range of from 2.00-7.00 wt %;
polyethylene in a range of from 10.00-19.00 wt %;
quaternium-90 montmorillonite in a range of from 0.50-1.00 wt %;
quaternium-90 sepiolite in a range of from 0.15-0.40 wt %;
silica in a range of from 0.01-0.07 wt %;
titanium dioxide in a range of from 3.00-9.00 wt %;
triethoxycaprylylsilane in a range of from 0.10-0.50 wt %;
trimethylsiloxysilicate in a range of from 0.10-0.90 wt %; and
undecylenic acid in a range of from 0.05-0.20 wt %.

* * * * *